(12) United States Patent
Venturini et al.

(10) Patent No.: US 11,547,448 B2
(45) Date of Patent: Jan. 10, 2023

(54) QUICK ATTACHMENT CLAMP FOR EXTERNAL FIXATION SYSTEMS

(71) Applicant: ORTHOFIX S.R.L., Bussolengo (IT)

(72) Inventors: Daniele Venturini, Povegliano Veronese (IT); Enrico Zandona, Quinto di Valpantena (IT); Chiara Dal Zovo, Caldiero (IT)

(73) Assignee: ORTHOFIX S.R.L., Bussolengo (IT)

( * ) Notice: Subject to any disclaimer, the term of this patent is extended or adjusted under 35 U.S.C. 154(b) by 0 days.

(21) Appl. No.: 16/969,824

(22) PCT Filed: Dec. 20, 2018

(86) PCT No.: PCT/EP2018/086088
§ 371 (c)(1),
(2) Date: Aug. 13, 2020

(87) PCT Pub. No.: WO2019/158262
PCT Pub. Date: Aug. 22, 2019

(65) Prior Publication Data
US 2020/0367935 A1    Nov. 26, 2020

(30) Foreign Application Priority Data
Feb. 16, 2018  (IT) .................. 102018000002749

(51) Int. Cl.
*A61B 17/64* (2006.01)
(52) U.S. Cl.
CPC ................ *A61B 17/6475* (2013.01)
(58) Field of Classification Search
CPC ..... A61B 17/66; A61B 17/6466; A61B 17/62; A61B 17/6414; A61B 17/645
(Continued)

(56) References Cited

U.S. PATENT DOCUMENTS 7,241,074 B2 *   7/2007   Thomke ............... A61B 17/645
                                                          24/545
9,155,562 B2 *  10/2015  Cremer ..................... F16B 2/12
(Continued)

FOREIGN PATENT DOCUMENTS

FR            2787697 A1       6/2000

OTHER PUBLICATIONS

Nternational Searching Authority/European Patent Office, "International Search Report," for PCT/EP2018/086088, dated Mar. 20, 2019, 3 pages.

(Continued)

*Primary Examiner* — Eduardo C Robert
*Assistant Examiner* — Tara Rose E Carter
(74) *Attorney, Agent, or Firm* — Haynes and Boone, LLP

(57) ABSTRACT

Clamp (1) for an external fixator, preferably of the quick attachment type, comprising: a plurality of attachments (2; 3) for blocking bars and/or bone screws; a connector (5), provided with an at least partially threaded stem (50), which passes through and connects in series said plurality of attachments (2; 3); at least one first attachment (2) comprising two arms (20; 21), connected by a C-shaped flexible bridge (22); said stem (50) passing through said first attachment (2) in an intermediate position between said flexible bridge (22) and the opposite free ends of said arms (20; 21); wherein, at the free ends, said arms (20; 21) define a screw housing seat (23) for a bone screw, said screw housing seat being selectively configurable, varying the deformation of the flexible bridge (22), to clamp bone screws having different diameter.

7 Claims, 16 Drawing Sheets

(58) Field of Classification Search
USPC .................................................. 606/53–59
See application file for complete search history.

(56) References Cited

U.S. PATENT DOCUMENTS

| | | |
|---|---|---|
| 2006/0039750 A1 | 2/2006 | Thomke et al. |
| 2007/0038217 A1 | 2/2007 | Brown et al. |
| 2008/0247818 A1 | 10/2008 | Oesch et al. |
| 2009/0306661 A1* | 12/2009 | Thomke ............... A61B 17/645 |
| | | 606/53 |
| 2011/0087226 A1* | 4/2011 | Murner .................... F16B 2/12 |
| | | 606/54 |

OTHER PUBLICATIONS

Nternational Searching Authority/European Patent Office, "Notification of Transmittal of the International Preliminary Report on Patentability," for PCT/EP2018/086088, dated May 6, 2020, 12 pages.

* cited by examiner

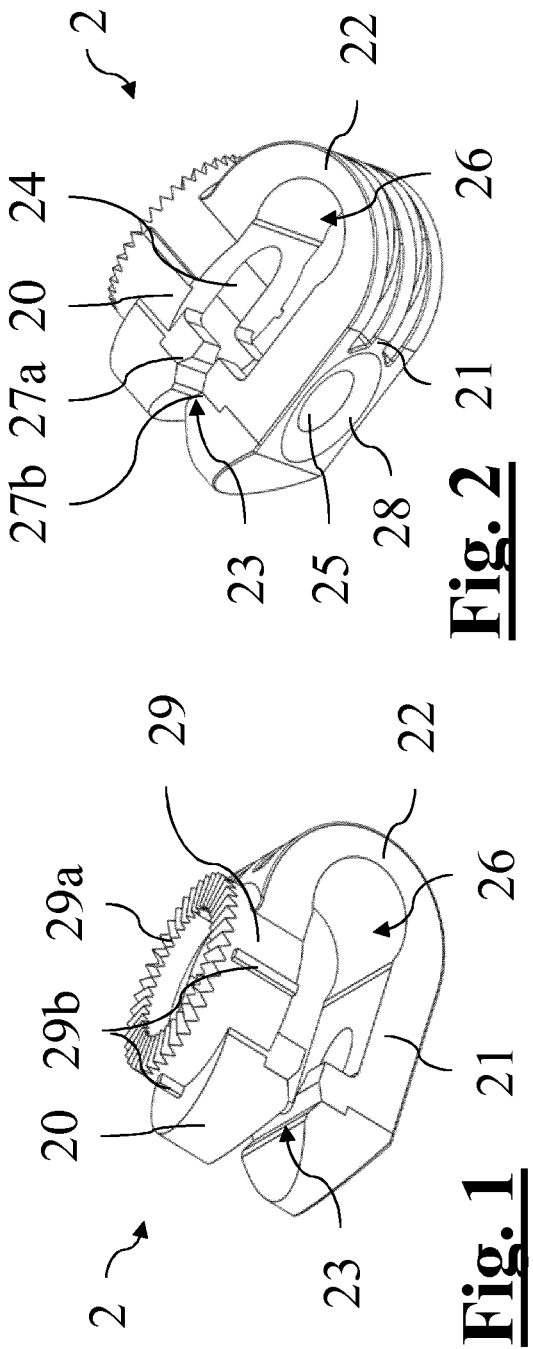
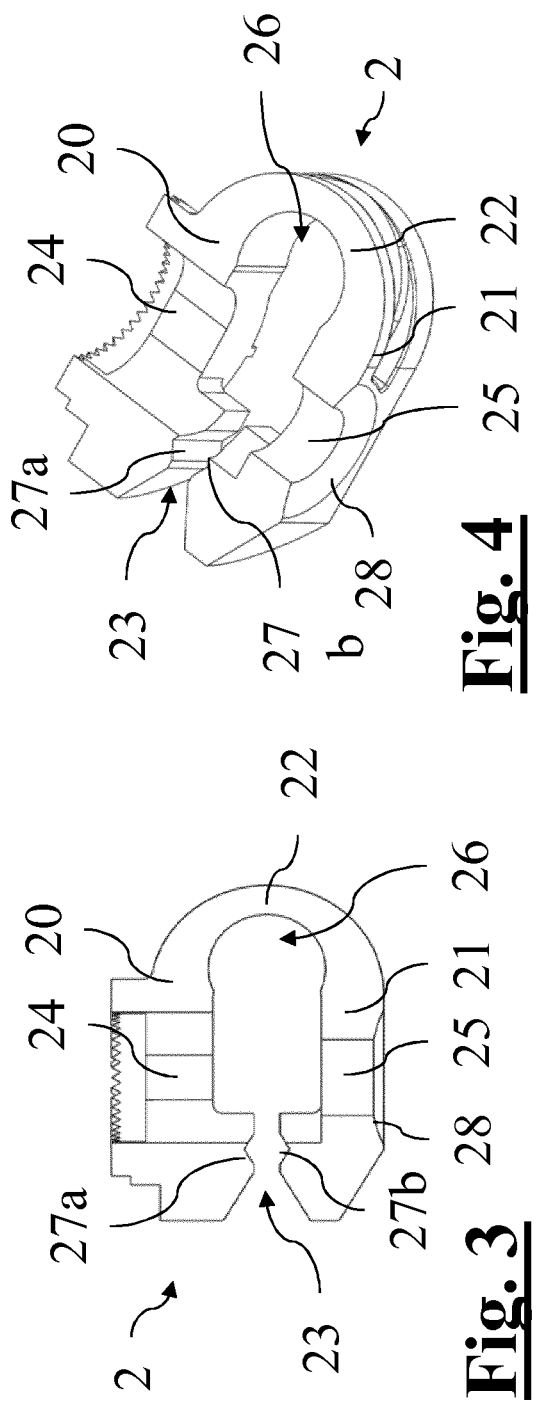

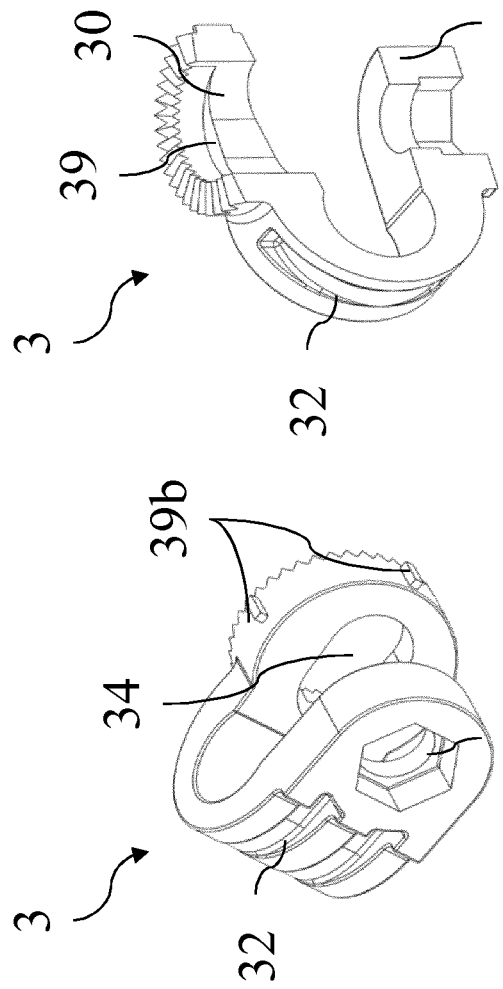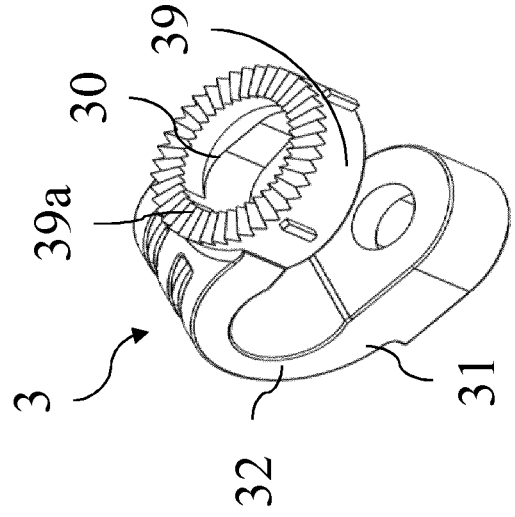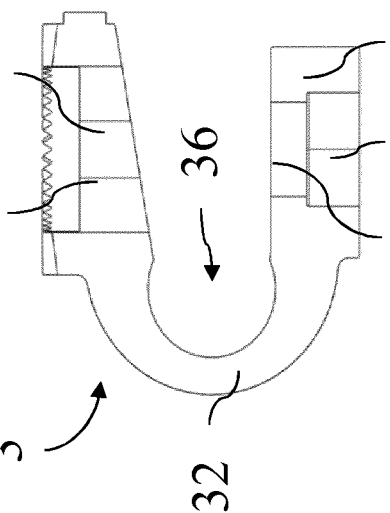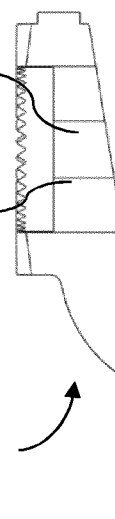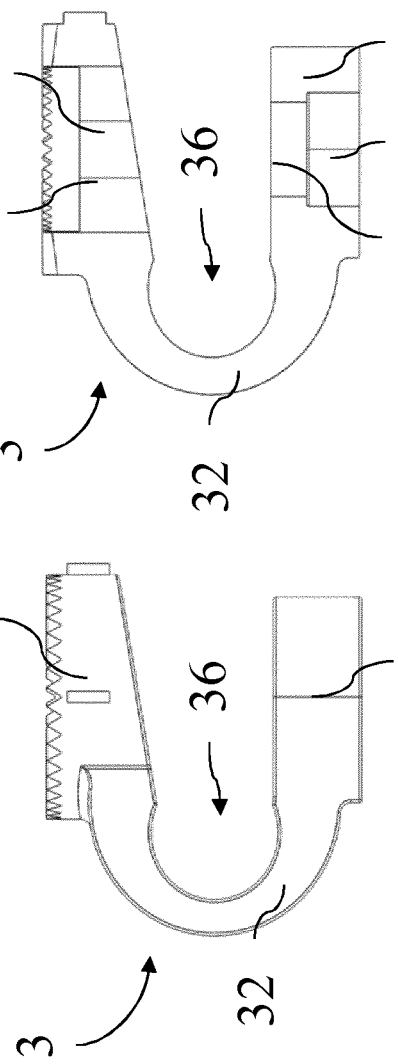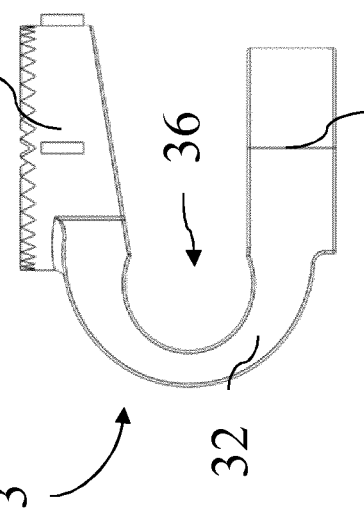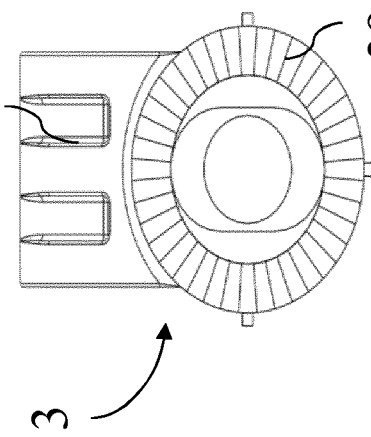

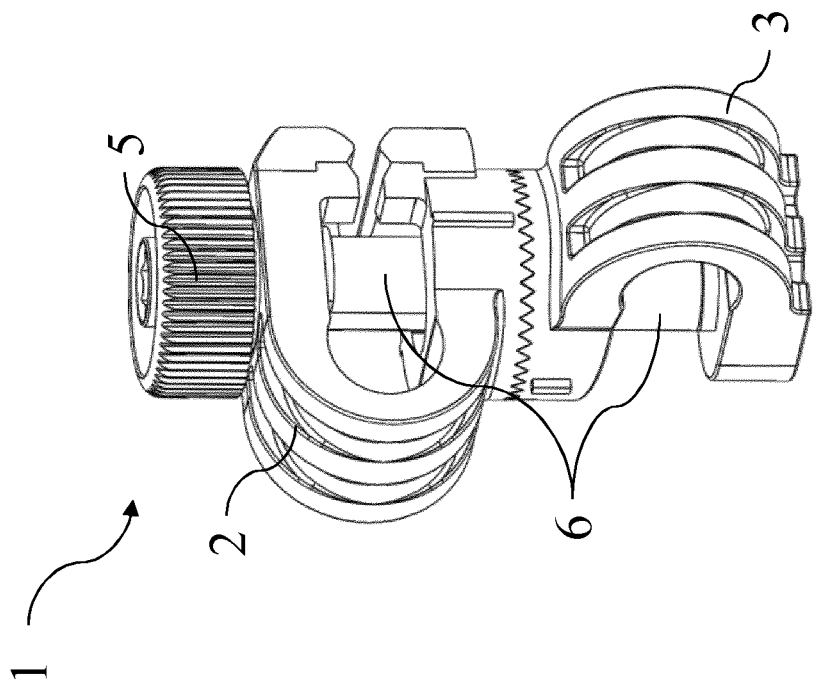
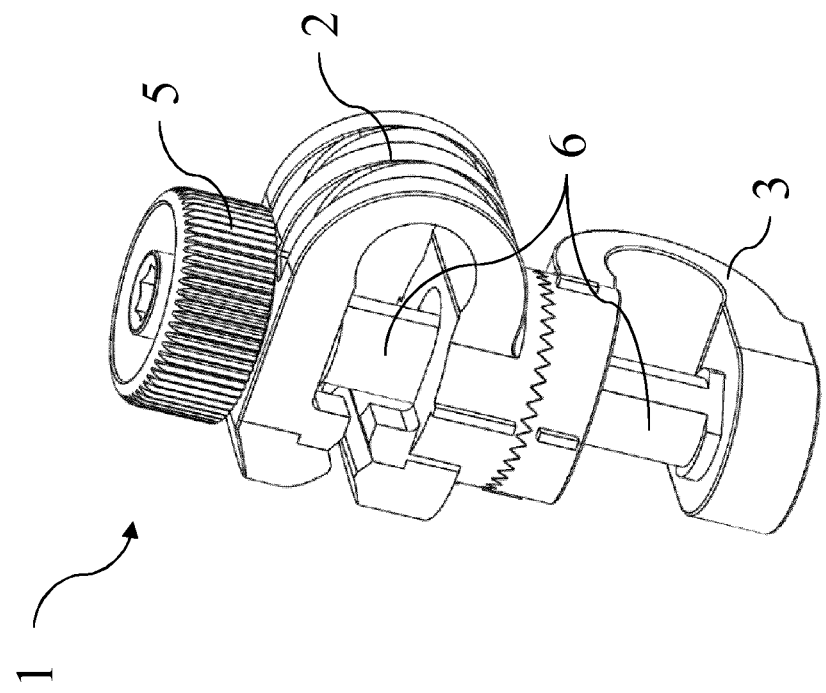

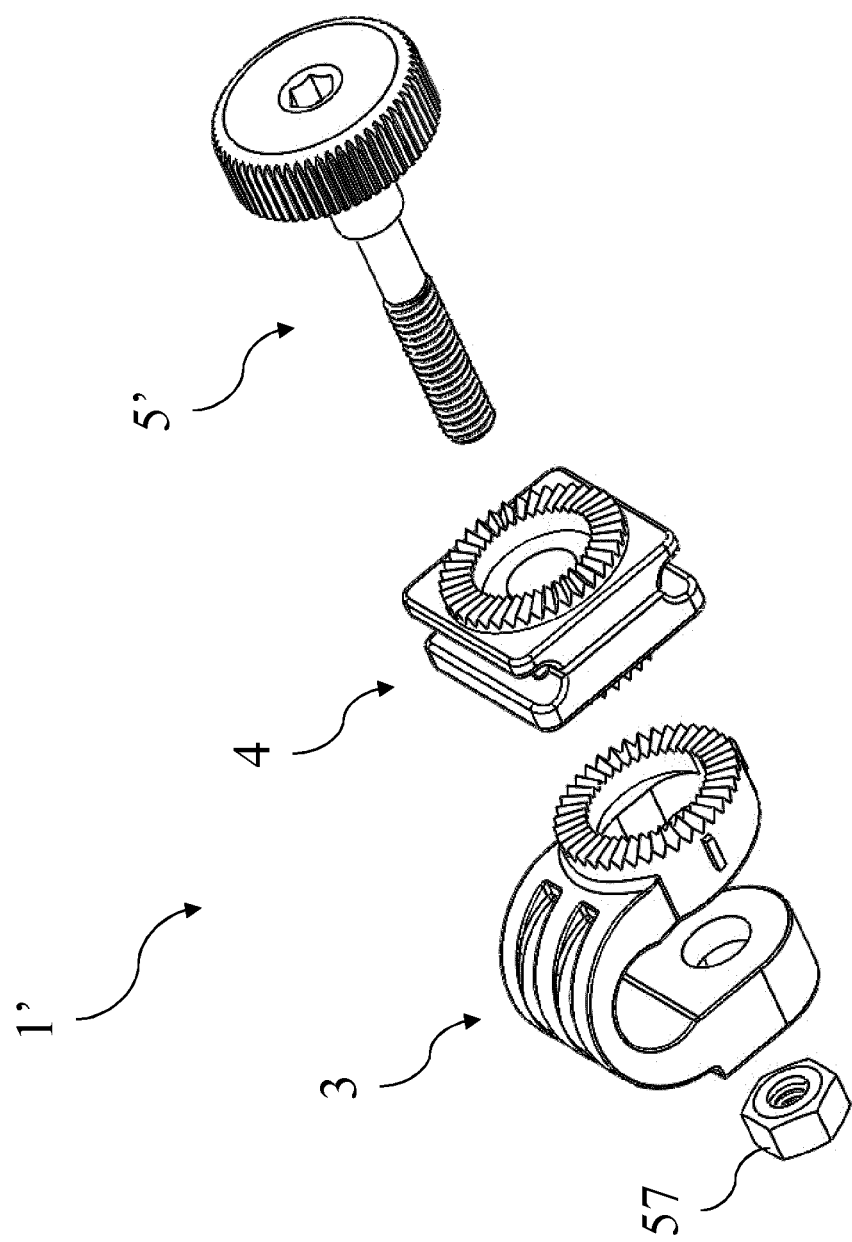

QUICK ATTACHMENT CLAMP FOR EXTERNAL FIXATION SYSTEMS

CROSS REFERENCE TO RELATED APPLICATIONS

The present application is the U.S. national phase of International Application No. PCT/EP2018/086088, filed Dec. 20, 2018, which designated the U.S. and claims priority to and the benefit of the Italian Application No. 102018000002749, filed Feb. 16, 2018, both of which are hereby incorporated by reference in their entirety as if fully set forth below in its entirety and for all applicable purposes.

DESCRIPTION

Technical Field

The present invention relates to a clamp for orthopedic applications, in particular intended for the coupling of the elements that constitute an external fixation system.

The invention, therefore, finds a useful application in the orthopedic surgery sector, in particular in trauma surgery.

Background Art

In orthopedics, external fastening techniques for stabilization, reduction and manipulation of bone segments are usually employed. Such techniques provide for the surgical application of a rigid exoskeleton, in its simplest form constituted by a set of bars articulated with one another by means of specific clamps, associated by means of screws to the patient's bone structure. Overall, the mechanic system adopted bears the name of external fixator.

The diversity of therapeutic needs that compose the hospital reality have contributed to the differentiation of various types of fixators, each one of which has technical and morphological features adapted for the use for which it is intended. So for certain applications, mostly trauma ones and on an urgent basis, the so-called quick fixators have been developed, precisely because they are characterized by fixation simplicity and speed.

Quick fixators comprise structural bars connected to clamps of different types: intended for connecting the bars with each other in the articulation points of the structure (bar-bar clamps); or placed to associate the bars to non-through screws anchored to the patient's bone (bar-screw clamps). All these clamps are elements of particular design criticality, as the opposite needs of ease of clamping and fixation stability have to be reconciled.

In this context, the market proposes a quick fixation system comprising a plurality of components that can be variously assembled to meet specific operating needs, illustrated by patent EP 1 056 407.

Such system, in particular, provides for both bar attachments, with a C-shaped configuration and relatively high axial bulk, and screw attachments with opposite plates, characterized by a reduced axial bulk with respect to bar attachments. Such attachments can be connected to one another by means of connection screws, which have to be conveniently selected of a measure adequate to the type of attachments to interconnect. The surgeon, therefore, has to compose two C-shaped attachments and a long screw to realize a bar-bar clamp; or a C-shaped attachment, a plates attachment and a short screw for obtaining a bar-screw clamp.

The system of the type described above, even if performing in a satisfactory manner the function for which it is intended, has some inconveniencies that are unsolved to date.

A first inconvenience concerns the scarce flexibility of use of the assembled clamp. The clamp's function is indeed rigidly dictated by the attachments that compose it; insofar as the multiplicity of components allows in theory a wide spectrum of functional combinations, in order to benefit from such possibility it is necessary to dispose in each operation of a complete panoply of components, comprising, for example, attachments for screws having different diameter adapted to the different anatomical sites.

Another inconvenience concerns the relative complexity of use of the system proposed above, deriving also from the high number of the components that can be potentially assembled. The need to select the correct structural elements for the desired single assembly (for example, as mentioned above, the long screw to realize a bar-bar clamp) can contribute to generate confusion in the surgeon.

Another inconvenience results from the scarcely ergonomic closing system, which requires that the operator performs a tightening of the connection screw with a hex key, even in the preliminary assembly phases.

The technical problem that is at the basis of the present invention is therefore that of solving at least some of the inconveniences described in the background art, and in particular to supply a clamp provided with a flexibility of application and an ease of use greater with respect to the devices known in the sector.

DISCLOSURE OF INVENTION

The idea of solution that is at the basis of the present invention is that of employing at least one attachment provided with a seat for screws of selectively variable dimension, so as to allow the blocking of bone screws of different diameter on a single clamp.

Said technical problem is therefore solved by a clamp for an external fixator, preferably of the quick attachment type, comprising: a plurality of attachments for the blocking of bars and/or bone screws; a connector, provided with an at least partially threaded stem, which passes through and connects in series said plurality of attachments; at least one first attachment of said plurality of attachments; at least one first attachment of said plurality of attachments comprising two arms, connected by a C-shaped flexible bridge; said stem passing through said first attachment in an intermediate position between said flexible bridge and the opposite free ends of said arms; wherein, at the free ends, said arms define a screw housing seat for a bone screw, said screw housing seat being selectively configurable, varying the deformation of the flexible bridge, to clamp bone screws having different diameter.

It is therefore the flexibility of the bridge that allows to modulate the clamping, drawing closer to or farther from each other the jaws obtained at the free end of the arms, which define the screw housing seat.

Preferably, the screw housing seat is adapted to allow the clamping of bone screws at least in the diameters of 4 mm, 5 mm and 6 mm, in order to serve the different anatomical sites or different dimensions of the bones (for example: 4 mm for wrist, foot; 5 mm for humerus, ankle; 6 mm for pelvis, femur, tibia).

In order not to hinder the deformation of the first attachment, at least one of said arms—preferably: the inner arm, namely the one that is found near another clamp and not towards the end of the structure—has an enlarged hole substantially wider with respect to the stem that passes through it. The hole, therefore, does not interfere with said stem as the deformation of the flexible bridge varies, at least in the range which corresponds to the desired variability for the diameter of the bone screws that can be clamped within said housing seat.

Moreover, also the inner arm will preferably have a passage hole for the stem. Such passage hole, even if it preferably has a width substantially matching that of the stem and therefore inferior to that of said enlarged hole, has anyway such a clearance as to allow the misalignments of the stem necessary to allow the desired bends of the attachment.

Advantageously, the connector can comprise a head integral with the stem and joined thereto with a concave surface; said external arm of the first attachment provides, at the outlet of said passage hole, for a convex seat adapted to contactingly match said concave surface even when the external arm is bent with respect to a condition of perpendicularity to the stem.

Preferably, the convex seat and the concave surface are spherical or cylindrical, in such a way as to guarantee the permanent contact between the surfaces in clamping conditions.

The screw housing seat is preferably defined by specular V-shaped profiles, which are facing and opposite one another, of the respective jaws integral with the free ends of the arms of the first attachment. Such morphology of the seat ensures linear contact stability on the bone screws of different diameter.

The housing seat presents also, preferably, conical insertion guiding slopes for the stem of the bone screws.

Advantageously, the first attachment can also provide for a bar housing seat for a bar of the external fixator. Such seat, using the morphology of the attachment, is defined by the inner profile, substantially shaped as an arc of a circle, of the flexible bridge.

The possibility of bar/screw combined attachment on the single first attachment guarantees an unknown flexibility of use of the clamp, and it also facilitates considerably the assembly since a single component can be selected for different uses.

Preferably, the arc of a circle that defines the bar housing seat is subtending an angle greater than 180°, to wrap the bar and increase the pressure on the same in the tightening configuration.

The connector, preferably, provides, at an end of the stem, for a coupling profile for a tightening tool—preferably a polygonal recess for a key head, for example a hexagonal recess for a hex key—and a tightening knob, with a diameter substantially greater with respect to said coupling profile, for the manual tightening of the connector.

The tightening knob can thus be advantageously used in a preliminary tightening phase, allowing an ergonomic assembly of the system.

Preferably, the tightening knob is defined by a peripheral collar separated by a cavity with respect to the coupling profile.

The tightening knob can also have, in particular on its own external peripheral surface, means to facilitate the manual gripping thereof, such as knurling or a surface coating in a highly gripping material, such as an elastomer.

The clamp, in addition to the first attachment already discussed, can comprise a second attachment provided only with a bar housing seat or, alternatively, a third attachment provided with one or more screw housing seats.

The material of the different attachments can be, but is not limited to, plastic (polyetherimide, polysulfone, polyarylamide, or similar ones) reinforced in glass or carbon fiber, in such a way as to conjugate mechanical resistance and sterilization with low costs.

For the connector simple stainless steel of the AISI 300 class can be employed, or an aluminum alloy or a titanium alloy.

It is noted also that the particularity of the design of the attachments and the absence of restricted tolerances suggest the adoption of three-dimensional printing techniques.

Further features and advantages will be shown to a greater extent in the detailed description below of a preferred but not limiting embodiment of the present invention, with reference to the annexed figures given as a not limiting example.

BRIEF DESCRIPTION OF DRAWINGS

FIG. 1 shows a perspective view of a first attachment making part of the clamp for an orthopedic fixator according to the present invention;

FIG. 2 shows a perspective view, according to a different angulation, of the attachment of FIG. 1;

FIG. 3 shows a lateral view, sectioned along a median plane, of the attachment of FIG. 1;

FIG. 4 shows a perspective view of the attachment of FIG. 1 sectioned along a median plane;

FIG. 5 shows a perspective view of a second attachment making part of the clamp for an orthopedic fixator according to the present invention;

FIG. 6 shows a perspective view, according to a different angulation, of the attachment of FIG. 5;

FIG. 7 shows a perspective view of the attachment of FIG. 5 sectioned along a median plane;

FIG. 8 shows a top view of the attachment of FIG. 5;

FIG. 9 shows a lateral view of the attachment of FIG. 5;

FIG. 10 shows a lateral view, sectioned along a median plane, of the attachment of FIG. 5;

FIG. 22 shows a perspective view of a clamp for an external fixator according to the present invention;

FIG. 23 shows a perspective view of the clamp of FIG. 22 according to a different angulation;

FIG. 31 shows a view of detached parts of the clamp of FIG. 29;

MODES FOR CARRYING OUT THE INVENTION

The preferred embodiment described below provides for a system comprising a plurality of components, compoundable for realizing different variants of clamp, identified in the annexed figures with references 1, 1' and 1".

Figure 32:
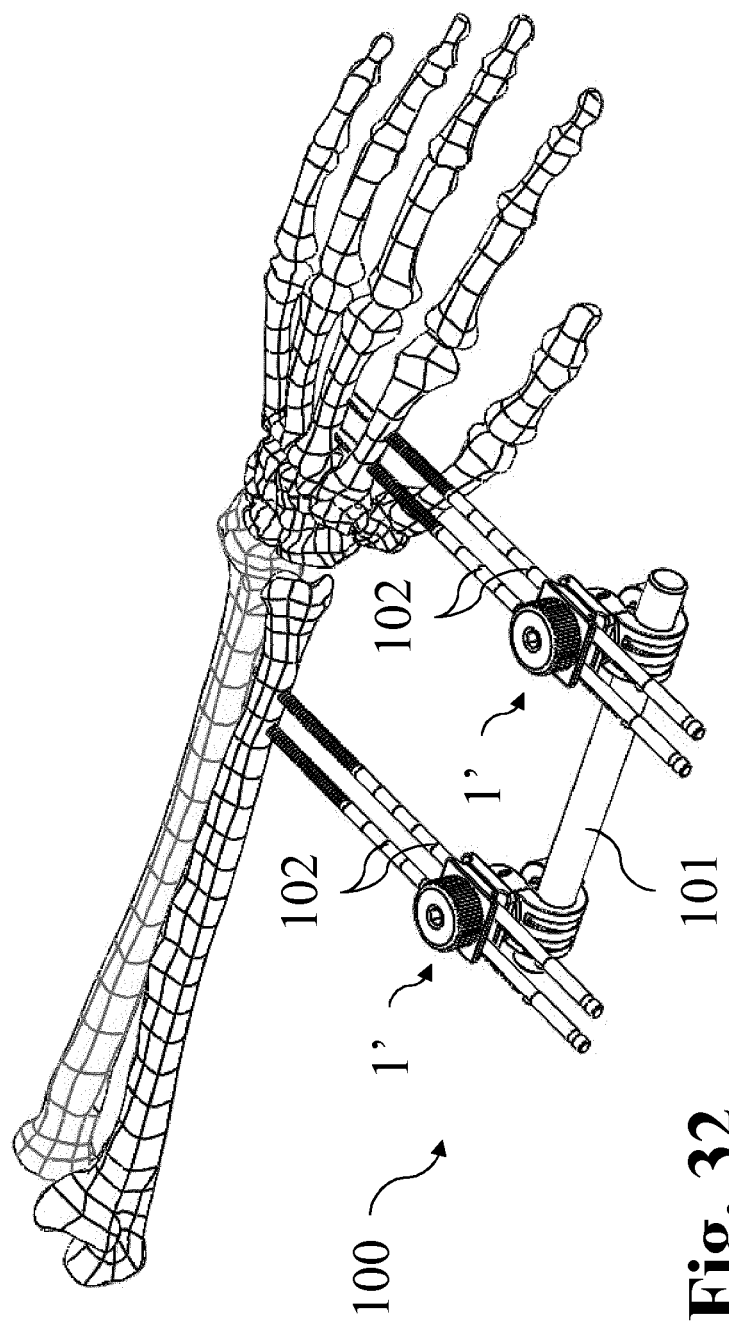
FIG. 32 shows an external fixator, comprising two clamps of the type in FIG. 29, matched to bone sites corresponding to a patient's wrist articulation.

Such clamp 1; 1'; 1", as specified in the previous discussion on the background art, has been projected to function as connecting element of an external orthopedic fixator 100, in particular of a quick fixator of the type illustrated in FIG. 32. The clamp 1; 1'; 1" is adapted to realize in a quick and efficient manner a temporary rigid connection between the two connecting bars 101 or between a bar 101 and a bone screw 102, of a diameter of 4 mm, 5 mm or 6 mm.

The first variant of clamp 1, illustrated in FIGS. 22-28, comprises a first attachment 2 and a second attachment 3, conveniently held together by a connector 5; the realization also provides for two spacers 6 placed respectively between the jaws of the first attachment 2 and of the second attachment 3. The spacers, in addition to performing a centering function, in the case of the second attachment 3 have also the role of effectively spacing in such a way as to limit the bend of the attachment, preventing all break risks.

Figure 14:
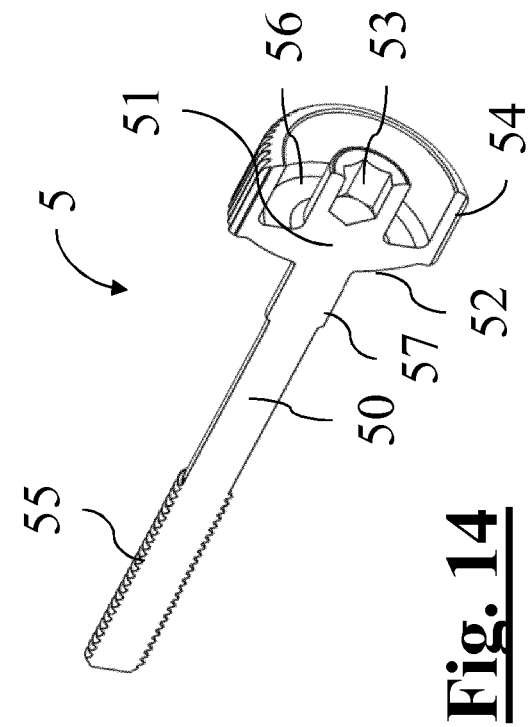
FIG. 14 shows a perspective view, sectioned along a median plane, of the connector of FIG. 13.
Figure 13:
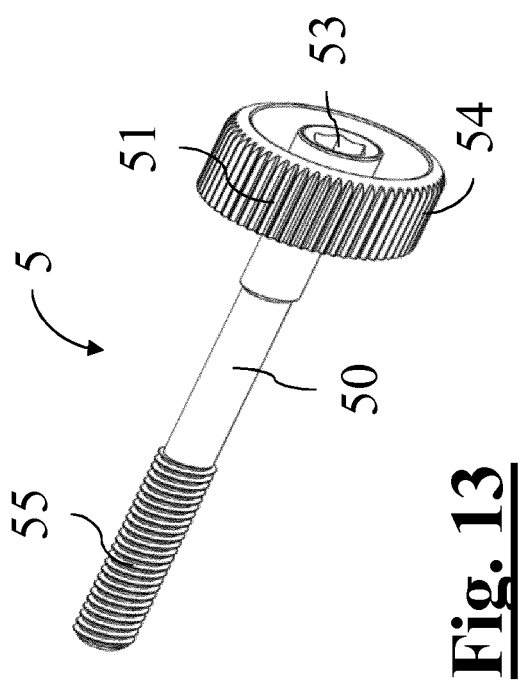
FIG. 13 shows a perspective view of a connector making part of the clamp for an orthopedic fixator according to the present invention.
Figure 15:
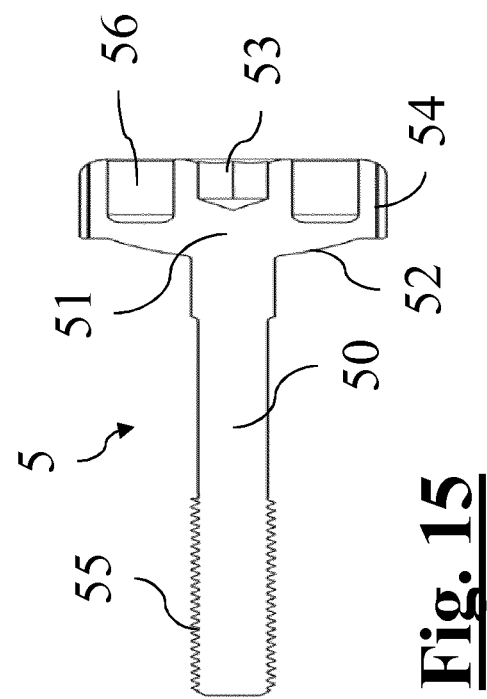
FIG. 15 shows a lateral view, sectioned along a median plane, of the connector of FIG. 13.

The connector 5, individually shown in FIGS. 13-15, comprises a stem 50 provided with a threaded end 55. The opposite end of the stem 50 provides for an enlarged collar 57 for reinforcement and centering, followed by a head 51 joined to the collar 57 by means of a concave surface 52, of substantially spherical shape.

The collar 57 has a diameter that allows to reduce the plays between stem 50 and passage holes of the attachments, favoring the joint of the reciprocal toothed surfaces to the interface of the attachments 2, 3.

The head 51 provides for an externally knurled ring nut, which defines a tightening knob 54. Internally, separated from the tightening knob by a cavity 56 open in the opposite direction to the stem 50, a coupling profile 53 is adopted, in this particular case a hexagonal recess for hex key.

The connector also provides for a tightening nut 57, adopted to be screwed on the threaded end 55, wrapping the attachments 2, 3 interposed between said elements. Moreover, it is to be noted that, in a variant of the project, the nut can be incorporated into the second attachment 3.

The first attachment 2, individually shown in FIGS. 1-4, is provided with two arms, which we will identify respectively as inner 20 and external 21 ones with respect to the overall structure of the assembled clamp 1. The arms 20, 21 are connected by a C-shaped flexible bridge 22, namely by an elastic hinge that allows the bend thereof outside of a rest configuration of reciprocal parallelism.

The flexible bridge 22 internally has a cylindrical surface, which develops on an arc slightly superior to 180°, to then join the internal planar surfaces of the two arms 20, 21. Such surface defines a bar housing seat 26, inside of which a connecting bar 101 of the external fixator 100 can be clamped.

At the opposite end with respect to the flexible bridge 22, the arms 20, 21 have respective jaws 27a, 27b. Such jaws 27a, 27b, thickened with respect to the rest of the arm, have opposite planar surfaces on which two V-shaped splines are obtained, extended transversally to the attachment. The two splines, faced one another, define a screw housing seat 23 which can contain screws of 4 mm, 5 mm or 6 mm, according to the bend given to the arms by the clamping of the connector 5.

The two arms 20, 21 further comprise respective holes 24, 25 adopted for the passage of the stem 50 of the connector 5. The hole realized on the inner arm 20 is an enlarged hole 24, of oval conformation extended in the sense of extension of the arm, with a substantially greater area with respect to the circumference of the stem 50. On the contrary, the passage hole 25 on the external arm 21 is circular and substantially proportional to the stem 50, still providing for a clearance sufficient to allow the bends of the attachment 2.

Outside of the hole of passage 25 a spherical flaring, namely a convex seat 28 for the concave surface 52 of the connector 5, is realized, which rests on it with substantial contact also in conditions of non-perpendicularity of the external arm 21 with respect to the stem 50.

Last, it is noted that the inner arm 20 is defined, in one of the intermediate portions thereof, by a cylindrical bush 29. Such bush exhibits a radial toothing 29a adopted to be constrained against a corresponding toothing of the juxtaposed attachment, guaranteeing the flexural stability of the clamp 1. Further, on the outer surface rises 29b are provided for, evenly spaced angularly, in the particular case at 90°, which can be used as angular references to guarantee the perpendicularity between connecting bars 101 and screw bones 102.

The second attachment 3, individually shown in FIGS. 5-10, has an analogous structure to that of the first attachment 2, except that it is not provided with jaws that define the seat for the bone screw. It is also provided with two arms, inner 30 and external 31 ones, with respect to the overall structure of the assembled clamp 1, connected to a C-shaped flexible bridge 32.

The flexible bridge 32 defines also in this case a bar housing seat 36, inside of which a connecting bar 101 of the external fixator 100 can be clamped.

The two arms 30, 31 comprise the respective holes 34, 35 adopted for the passage of the stem 50 of the connector 5. The hole realized on the inner arm 30 is an enlarged hole 34 analogous to that obtained on the inner arm 20 of the first attachment 2. The passage hole 35 on the external arm 21 is also here substantially proportional to the stem 50, providing for a clearance sufficient to allow the bends of the attachment 3.

Outside of the passage hole 35 a hexagonal recess 38 is realized for the housing of the clamping nut 57, which, as previously mentioned, can be incorporated in the attachment 3 itself during the printing process.

Also in this case the inner arm 30 is defined, in a terminal and not intermediate portion, by a cylindrical bush 39. Such bush exhibits a radial toothing 39a adopted to be constrained against the toothing of the juxtaposed attachment and rises 39b of reference spaced of 90° one from another.

Figure 19:
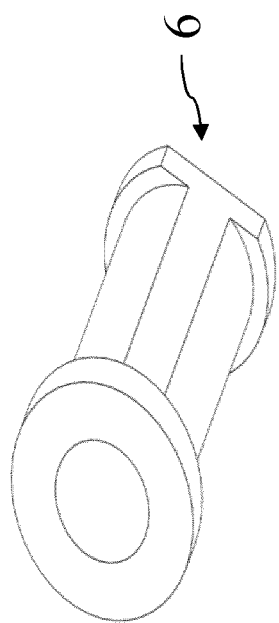
FIG. 19 shows a perspective view of a spacer making part of the clamp for an orthopedic fixator according to the present invention.
Figure 20:
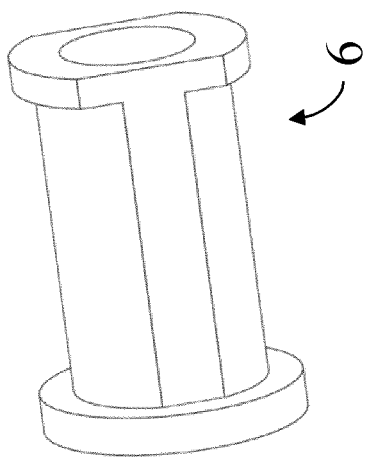
FIG. 20 shows a perspective view, according to a different angulation, of the spacer of FIG. 19.
Figure 21:
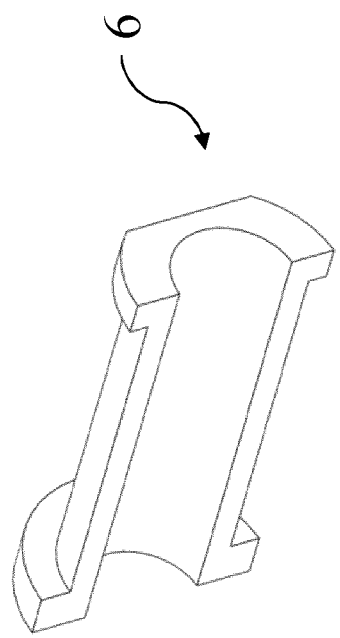
FIG. 21 shows a perspective view, sectioned along a median plane, of the spacer of FIG. 19.
Figure 24:
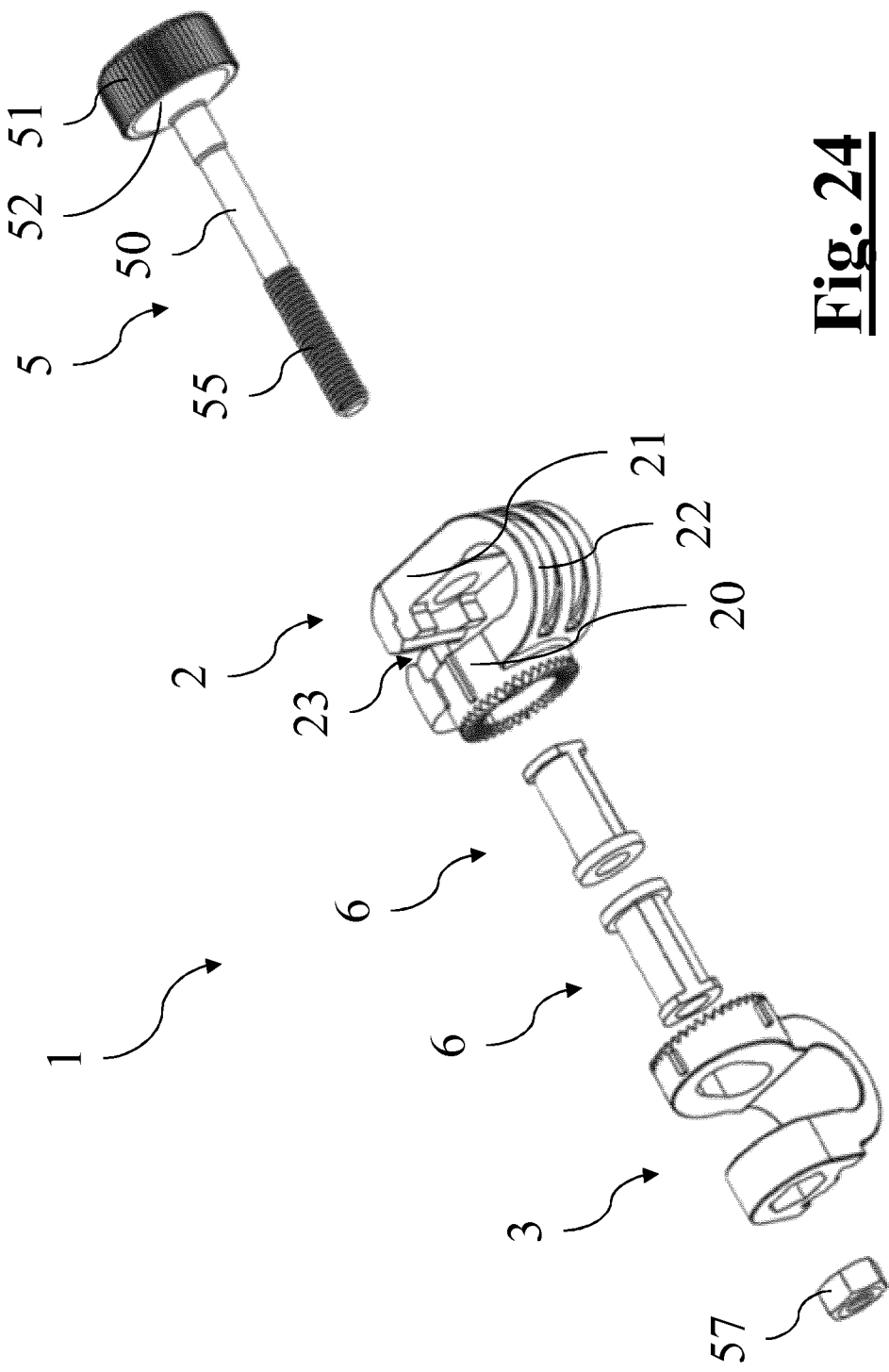
FIG. 24 shows a view of detached parts of the clamp of FIG. 22.
Figure 25:
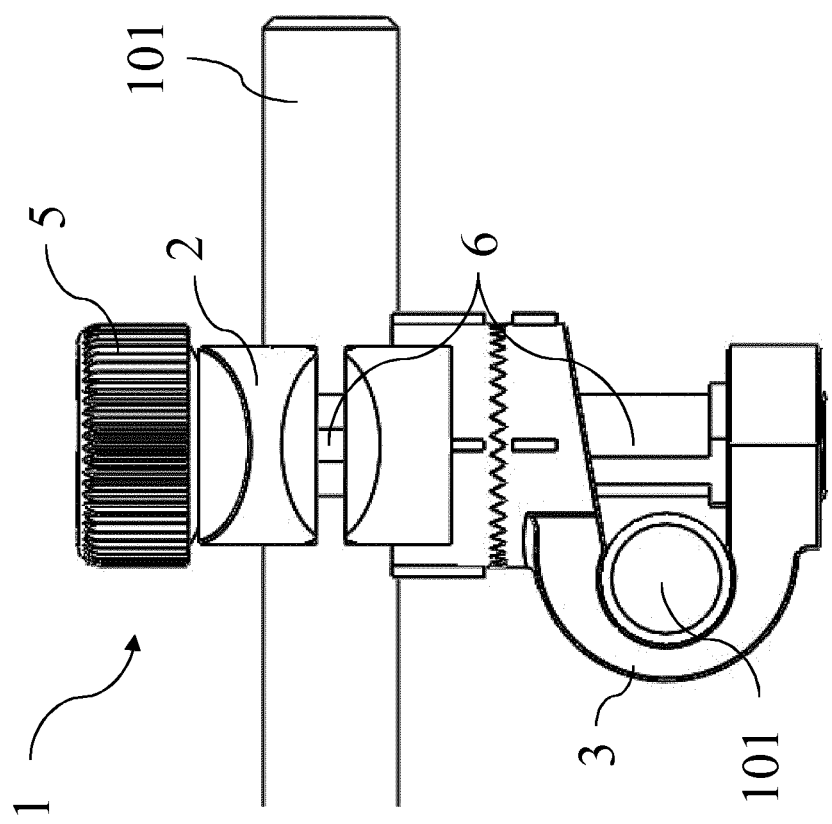
FIG. 25 shows a front view of the clamp of FIG. 22 applied to a bar of an external fixator.
Figure 26:
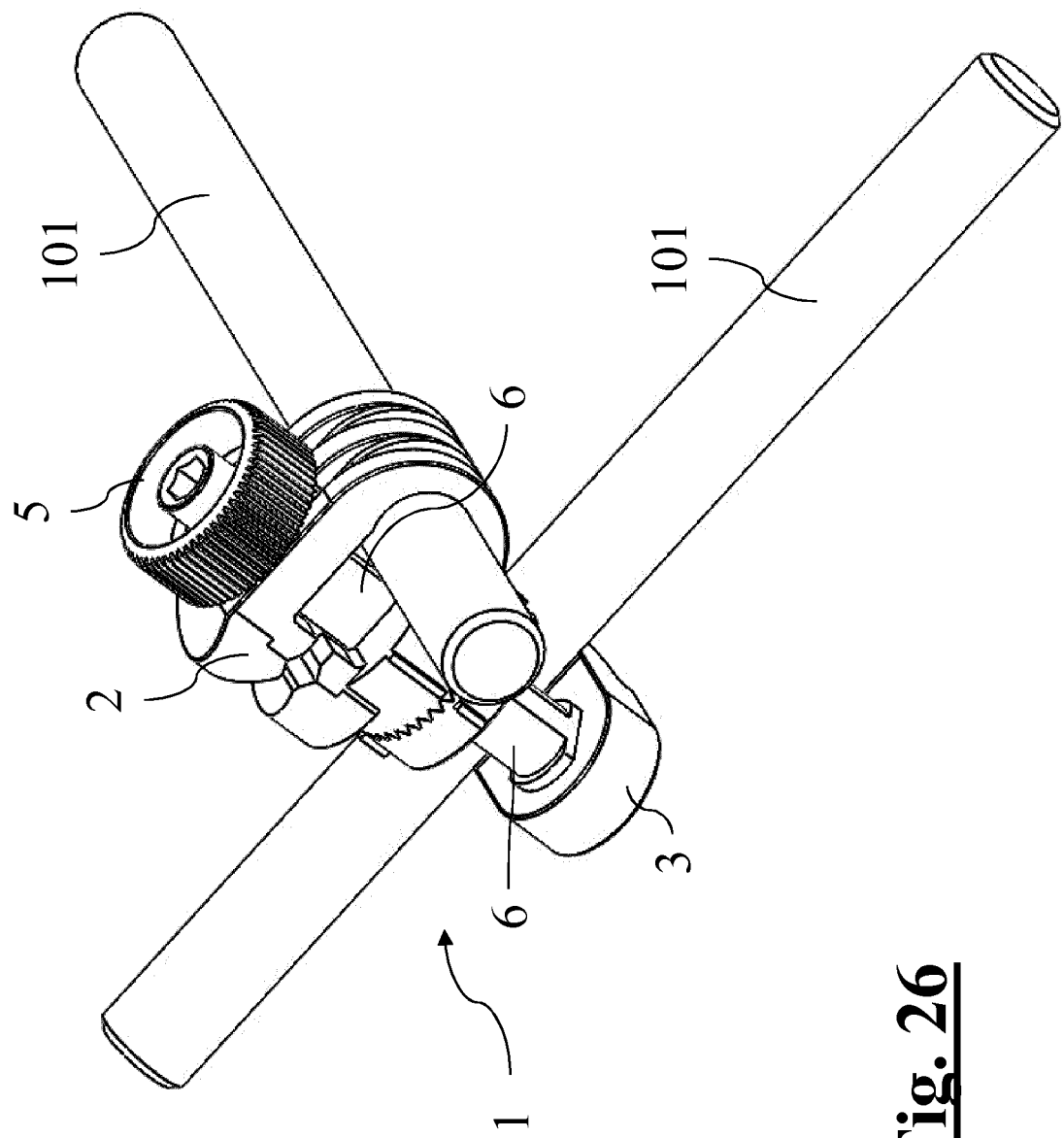
FIG. 26 shows a perspective view of the clamp of FIG. 22 applied to two bars of an external fixator matched orthogonally one to another.
Figure 27:
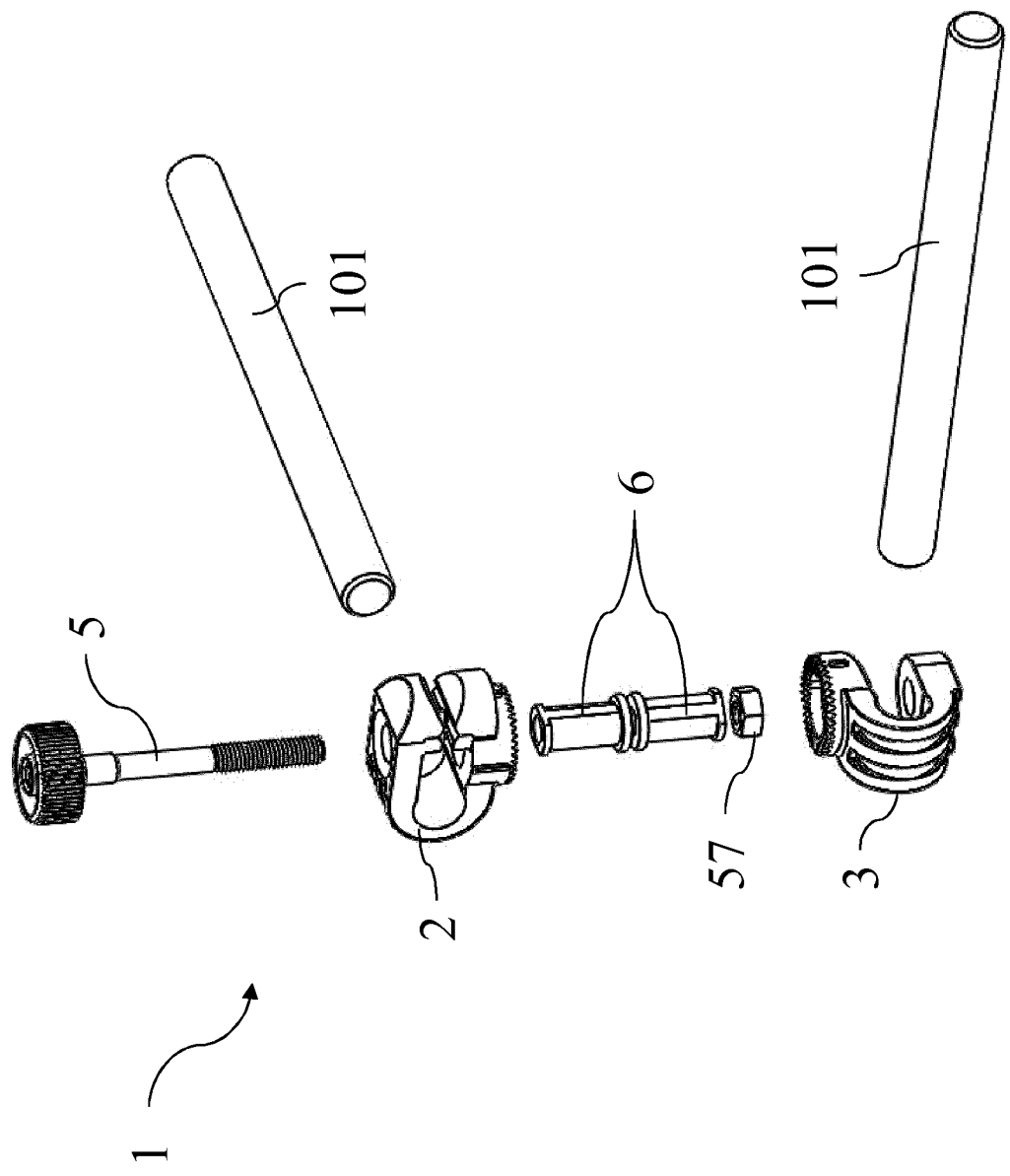
FIG. 27 shows a view of detached parts of the configuration of FIG. 26.
Figure 28:
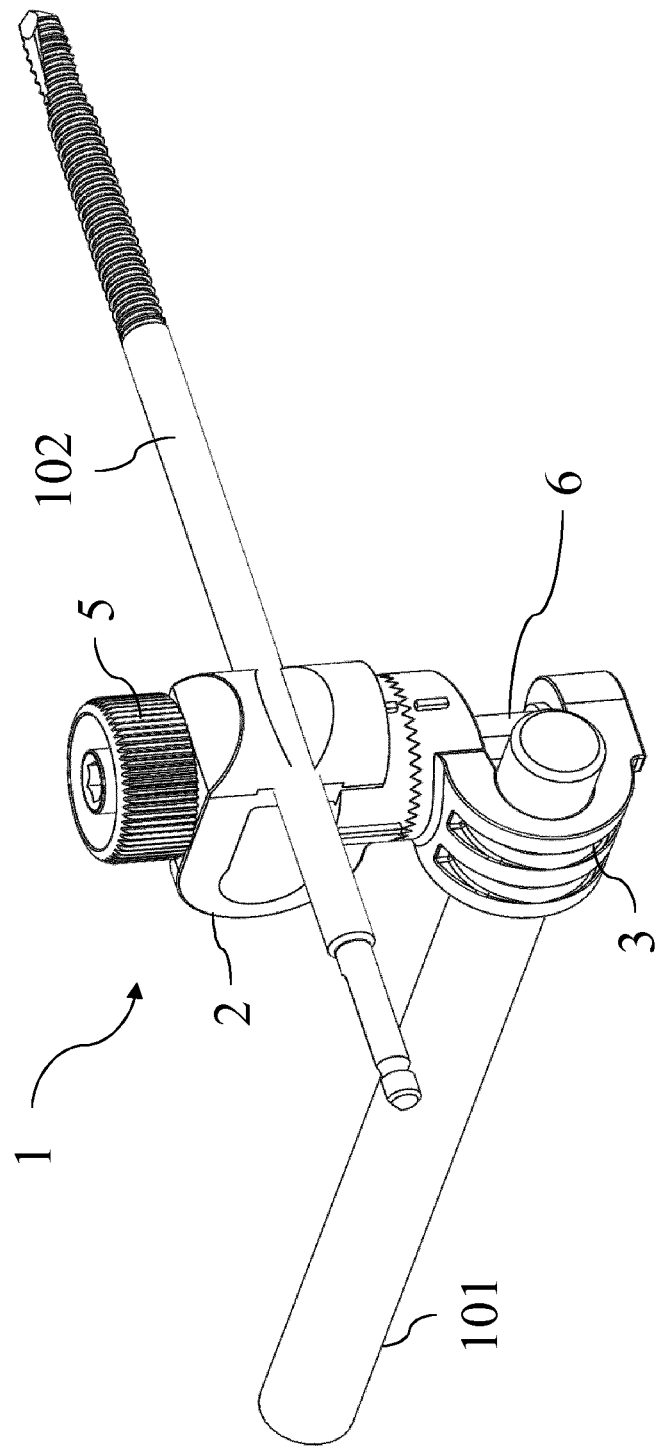
FIG. 28 shows a perspective view of the clamp of FIG. 22 applied to a bar of an external fixator matched orthogonally to a bone screw.

The spacers 6, individually shown in FIGS. 19-21, are substantially cylindrical sleeves, provided with opposite flanges and lateral flattenings, adopted to ring themselves on the stem 50, separating the arms 20, 21; 30, 31 of a single attachment 2; 3; or, as mentioned above, they can also have a mere centering function, in particular when used in combination with the first attachment 2.

The second variant of clamp 1', illustrated in FIGS. 29-32, comprises a second attachment 3 of the previously described type and a third attachment 4, held together by a connector 5'.

Figure 11:
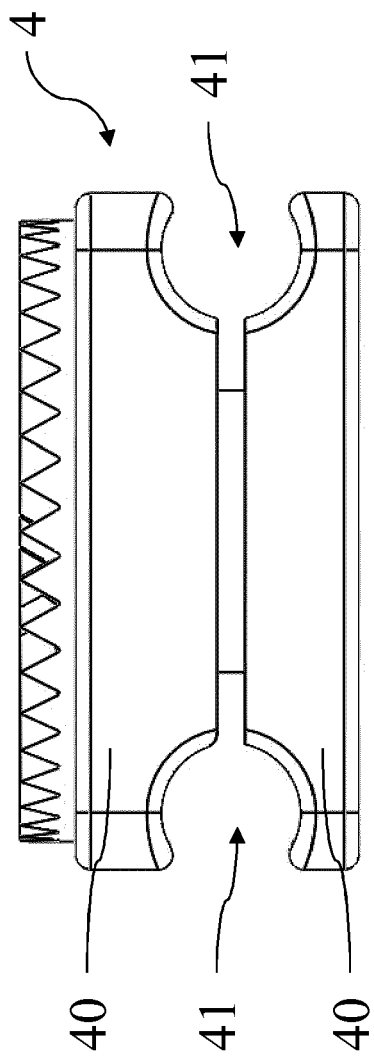
FIG. 11 shows a front view of a third attachment of the clamp for an orthopedic fixator according to the present invention.
Figure 12:
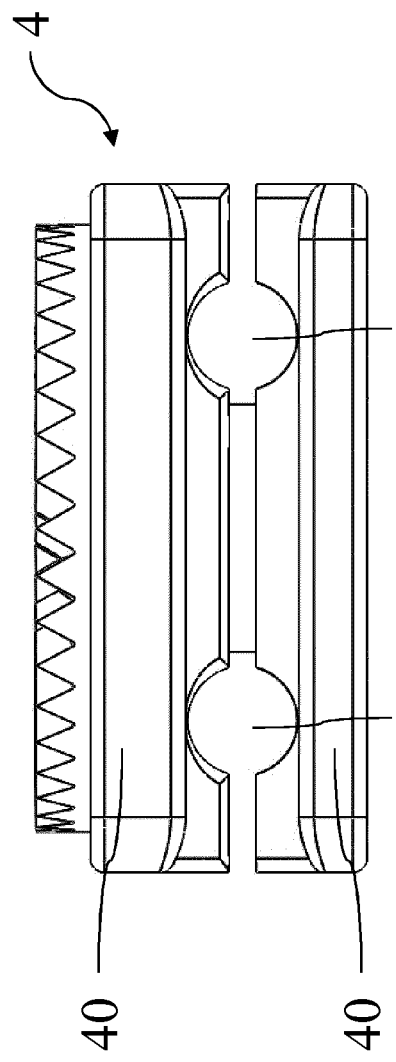
FIG. 12 shows a lateral view of the third attachment of FIG. 11.

The third attachment 4, individually illustrated in FIGS. 11 and 12, is composed by two plates 40 substantially counter formed which define to the interface thereof splines and lateral grooves for holding bone screws 102. The splines and/or lateral grooves intersect one another at 90°, and define two pairs of seats for bone screws 102 having different diameter and/or different center to center distance. In particular, in this particular case: in a front-rear direction the plates 40 define two lateral grooves 41 for holding screws of diameter 5 mm or 6 mm, with a center to center distance around the 20 mm; in a right-left direction the plates define two passage holes 42 for holding screws of diameter 4 mm with a center to center distance around the 14 mm.

Figure 17:
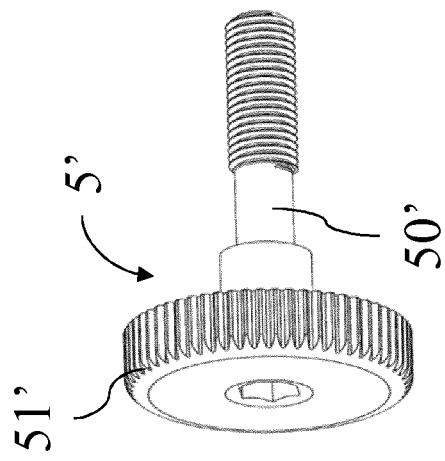
FIG. 17 shows a perspective view, according to a different angulation, of the connector of FIG. 16.
Figure 16:
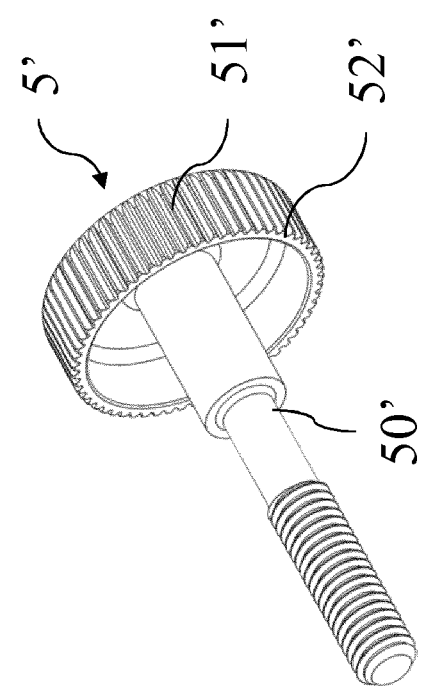
FIG. 16 shows a perspective view of an alternative connector for an orthopedic fixator of the type according to the present invention.
Figure 18:
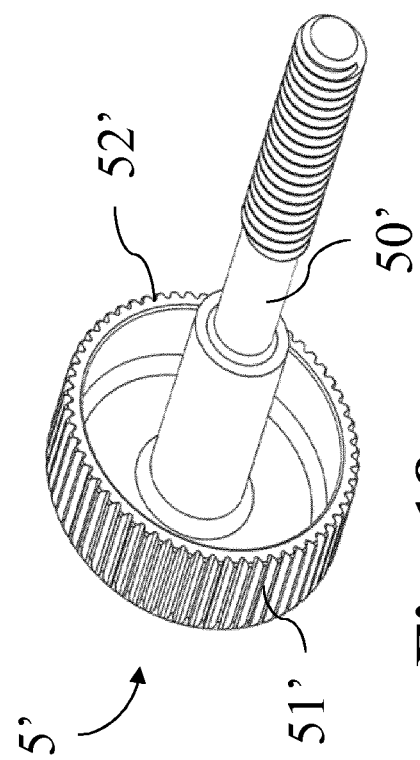
FIG. 18 shows a perspective view, according to another different angulation, of the connector of FIG. 16.
Figure 30:
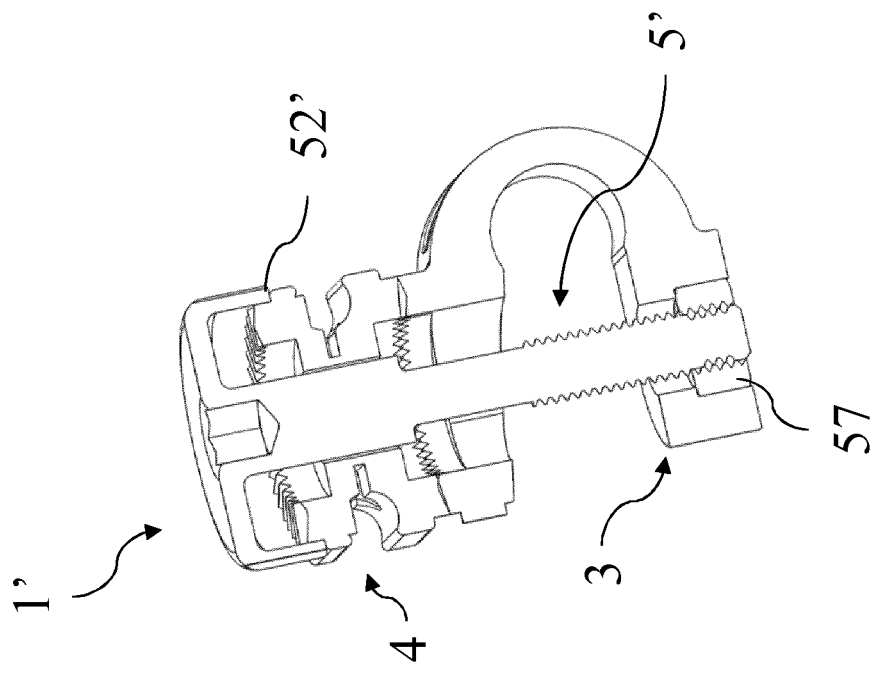
FIG. 30 shows a perspective view, sectioned according to a median plane, of the clamp of FIG. 29.
Figure 29:
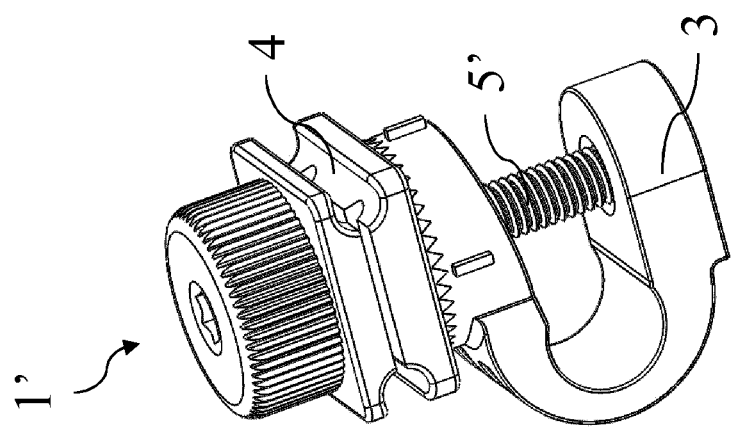
FIG. 29 shows a perspective view of a first variant of clamp for an external fixator that can be realized by assembling components of the clamp according to the present invention.

The connector 5' for this type of clamp 1', individually illustrated in FIGS. 16-18, is slightly different with respect to the previously discussed one. In fact, it presents a stem 50' of an inferior length and a head profile 51' with only circumferential abutment 52' to be loaded only on the external part of the third attachment 4 where the profile is realized as a yielding cantilever. In particular, as shown in FIG. 30, such circumferential abutment 52' does not impinge on the radial toothing of the third attachment 4.

Figure 33:
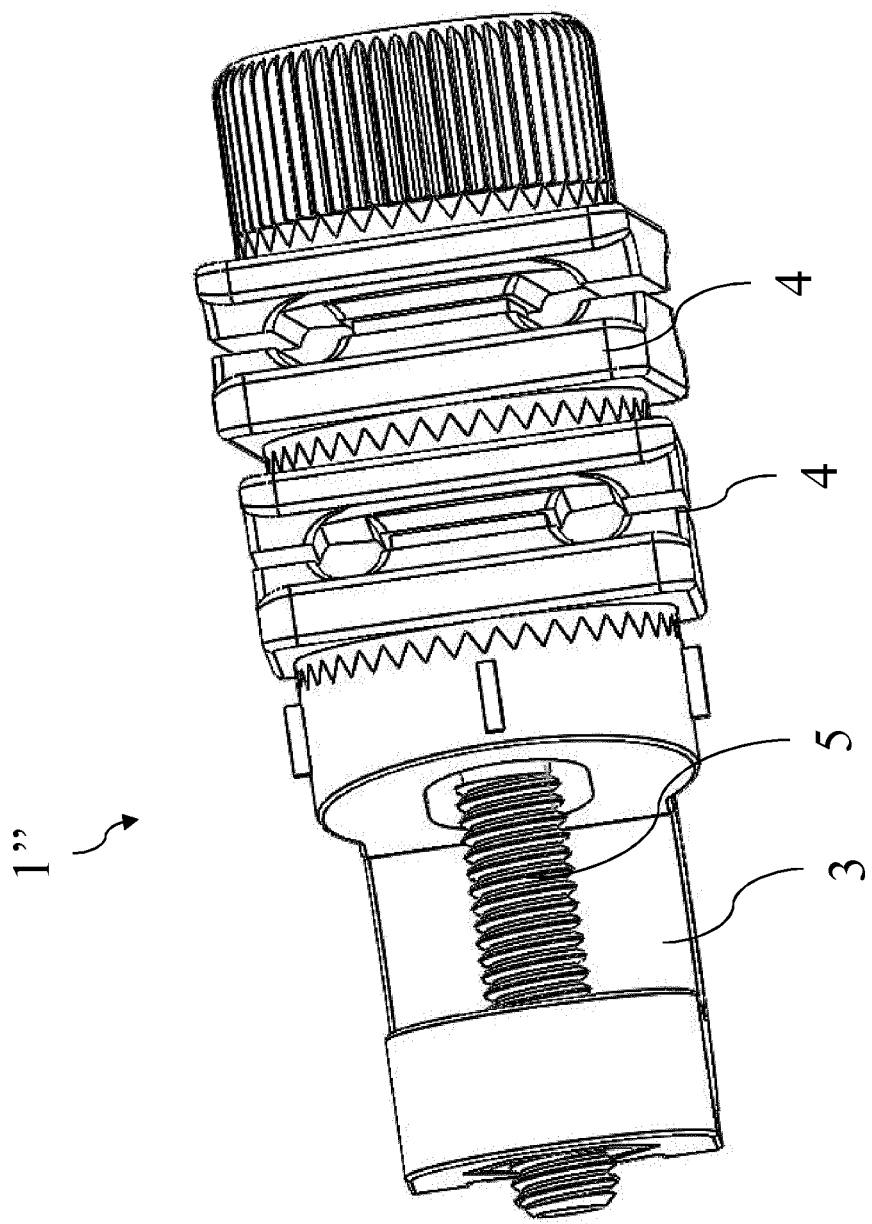
FIG. 33 shows a second variant of clamp for an external fixator that can be realized by assembling components of the clamp according to the present invention.

The third variant of clamp 1", illustrated in FIG. 33, comprises a second attachment 3 and two third attachments 4 overlapped one to another, held together by a connector 5.

Obviously, to the invention described above an expert of the sector, in order to meet temporary and specific needs, can introduce several amendments and variants, all however contained in the field of protection of the invention as defined by the following claims.

The invention claimed is:

1. Clamp for an external fixator, comprising:
a plurality of attachments for locking bars and/or bone screws; a connector provided with an at least partially threaded stem, which passes through and connects in series said plurality of attachments; at least one first attachment of said plurality of attachments comprising two arms, connected by a C-shaped flexible bridge; said stem passing through said first attachment in an intermediate position between said flexible bridge and the opposite free ends of said arms wherein, at the free ends, said arms define a screw housing seat for a bone screw; wherein said screw housing seat is selectively configurable, varying the deformation of the flexible bridge, to clamp bone screws having different diameter; wherein said screw housing seat allows at least the clamping of bone screws with diameters of 4 mm, 5 mm and 6 mm; wherein said first attachment also provides for a bar housing seat for a bar of the external fixator; wherein said bar housing seat is defined by an inner profile, substantially shaped as an arc of a circle, of the flexible bridge of the first attachment, said arc of a circle subtending an angle greater than 180°; and wherein at least one of said arms of the first attachment has an enlarged hole substantially wider with respect to the stem that passes through it, so that it does not interfere with said stem as the deformation of the flexible bridge varies, at least in the range which corresponds to the desired variability for the diameter of the bone screws that can be clamped within said housing seat.

2. Clamp according to claim 1, wherein said screw housing seat is defined by specular V-shaped profiles, which are facing and opposite one another, of respective jaws integral with the free ends of the arms of the first attachment.

3. Clamp according to claim 1, wherein said connector provides, at an end of the stem, for a coupling profile for a tightening tool and a tightening knob, with a diameter substantially greater with respect to said coupling profile, for the manual tightening of the connector.

4. Clamp according to claim 3, wherein said tightening knob has means to facilitate the manual gripping thereof, such as knurling or surface coating.

5. Clamp according to claim 1, further comprising a second attachment provided with a bar housing seat or a third attachment provided with one or more screw housing seats.

6. Clamp according to claim 1, wherein the arm of the first attachment that has the enlarged hole is an inner arm with respect to the overall structure of the clamp, namely it is the arm juxtaposed to a second attachment.

7. Clamp according to claim 6, wherein an external arm of said first attachment has a passage hole for said stem; said connector comprises a head integral with the stem and joined thereto with a concave surface; said external arm provides, at an outlet of said passage hole, for a convex seat adapted to contactingly match said concave surface even when the external arm is bent with respect to a condition of perpendicularity to the stem.

* * * * *